(12) United States Patent
Petschke et al.

(10) Patent No.: US 10,499,869 B2
(45) Date of Patent: Dec. 10, 2019

(54) APPARATUS AND METHOD FOR MATERIAL DECOMPOSITION OF SPECTRALLY RESOLVED PROJECTION DATA USING SINGLES COUNTS

(71) Applicants: Kabushiki Kaisha Toshiba, Minato-ku (JP); Toshiba Medical Systems Corporation, Otawara (JP)

(72) Inventors: Adam Petschke, Vernon Hills, IL (US); Gin-Chung Wang, Lincolnshire, IL (US); Yu Zou, Naperville, IL (US)

(73) Assignee: Toshiba Medical Systems Corporation, Otawara-shi (JP)

( * ) Notice: Subject to any disclaimer, the term of this patent is extended or adjusted under 35 U.S.C. 154(b) by 649 days.

(21) Appl. No.: 15/017,310

(22) Filed: Feb. 5, 2016

(65) Prior Publication Data
US 2017/0224299 A1    Aug. 10, 2017

(51) Int. Cl.
*A61B 6/00* (2006.01)
*A61B 6/03* (2006.01)

(52) U.S. Cl.
CPC ............ *A61B 6/5211* (2013.01); *A61B 6/032* (2013.01); *A61B 6/4241* (2013.01); *A61B 6/482* (2013.01)

(58) Field of Classification Search
CPC .. A61B 6/00; A61B 6/03; A61B 6/032; A61B 6/4241; A61B 6/482; A61B 6/5211; G01N 23/08; G01N 23/083; G01N 23/087; G01N 23/046; G01T 1/2928; G06T 11/005; G06T 11/008
USPC .................. 378/4, 5, 19, 98.8, 98.9, 901
See application file for complete search history.

(56) References Cited

U.S. PATENT DOCUMENTS

| 7,865,005 B2 | 1/2011 | Ye et al. |
| 8,338,791 B2 | 12/2012 | Proksa et al. |
| 2012/0027274 A1 | 2/2012 | Farahani et al. |

*Primary Examiner* — Jurie Yun
(74) *Attorney, Agent, or Firm* — Oblon, McClelland, Maier & Neustadt, L.L.P.

(57) ABSTRACT

A method and apparatus is provided to decompose spectral computed tomography (CT) projection data into material components using singles-counts and total-counts projection data. The singles-counts projection data more accurately solves the material decomposition problem, but can produce multiple results only one of which is correct. The total-counts projection data generates a unique result, but is less precise. The total-counts projection data is used to disambiguate the multiple results of the singles-counts projection data providing a unique results that is also precise. The unique and precise material decomposition can be achieved by limiting a search region for the singles-counts result to a neighborhood surrounding the total-counts result, choosing a singles-counts result that is closest to the total-counts result, choosing a singles-counts result that minimizes a total-counts cost function, or using a combined cost function that includes a singles-counts projection data and energy-integrated projection data.

20 Claims, 11 Drawing Sheets

APPARATUS AND METHOD FOR MATERIAL DECOMPOSITION OF SPECTRALLY RESOLVED PROJECTION DATA USING SINGLES COUNTS

FIELD

This disclosure relates to decomposing spectral computed tomography (CT) projection data into material components, and more particularly, to material decomposition of spectral CT projection data using single-photon detection events to improve the decomposition into the material components.

BACKGROUND

Computed tomography (CT) systems and methods are widely used, particularly for medical imaging and diagnosis. CT systems generally create projection images through a subject's body at a series of projection angles. A radiation source, such as an X-ray tube, irradiates the body from one side. Images of the subject's body can be reconstructed from the projection data (i.e., the projection images acquired a various projection angles), using various reconstruction techniques such as filtered back-projection, iterative reconstruction, etc.

Conventionally energy-integrating detectors have been used to measure CT projection data. Now, recent technology developments are making, photon-counting detectors a feasible alternative to conventional energy-integrating detectors. Photon-counting detectors have many advantages including their capacity for performing spectral CT, wherein the photon-counting detectors resolve the counts of incident X-rays into spectral components referred to as energy bins. Each energy bin has a different spectral window within the energy spectrum of the X-ray beam, such that collectively the energy bins span the energy spectrum of the X-ray beam. Since spectral CT involves the detection of transmitted X-rays at two or more energy levels, spectral CT generally includes dual-energy CT by definition.

Photon-counting detectors can use semiconductors with fast response times. This fast response time enables photon-counting detectors to resolve in time individual X-ray detection events. However, at high X-ray flux rates indicative of clinical X-ray imaging, multiple X-ray detection events on a single detector can occur within the detector's time response—a phenomenon called pileup. Left uncorrected, pileup, detector nonlinearities, and other artifacts of the projective imaging process can degrade reconstructed images from photon-counting detectors.

On the other hand, when these effects are corrected, spectral CT has many advantages over conventional CT. Many clinical applications can benefit from spectral CT technology, including improved material differentiation and beam hardening corrections. Moreover, compared with non-spectral CT, spectral CT extracts complete tissue characterization information from an imaged object.

One challenge for more effectively using semiconductor-based photon-counting detectors for spectral CT is performing the material decomposition of the projection data in a robust and efficient manner. For example, correction of pileup and nonlinearities in the X-ray detection process can be imperfect, and these imperfections degrade the material components resulting from the material decomposition.

To avoid the biases and errors associated with pileup, post-selection and/or pileup rejection can be used to isolate those detection events in which a single X-ray photon was detected within a detection time window and exclude the multi-photon detection events. The projection data corresponding to only single-photon detection events is called singles-counts projection data, in contrast to the total-counts projection data.

One drawback of the singles-counts projection data is that the input X-ray flux resulting in a given number of singles counts is multi-valued, resulting in a multi-valued material decomposition. Thus, material decomposition using singles counts (as opposed to total counts data) can generate ambiguous results. On the other hand, material decomposition using total-counts projection data generates a unique solution, but this unique solution suffers from biases, increased noise, and other errors introduced by pileup. Conventional methods do not simultaneously achieve the enhanced precision of material decomposition using singles counts together with the uniqueness of material decomposition using the total counts.

BRIEF DESCRIPTION OF THE DRAWINGS

A more complete understanding of this disclosure is provided by reference to the following detailed description when considered in connection with the accompanying drawings, wherein.

DETAILED DESCRIPTION

Figure 1:
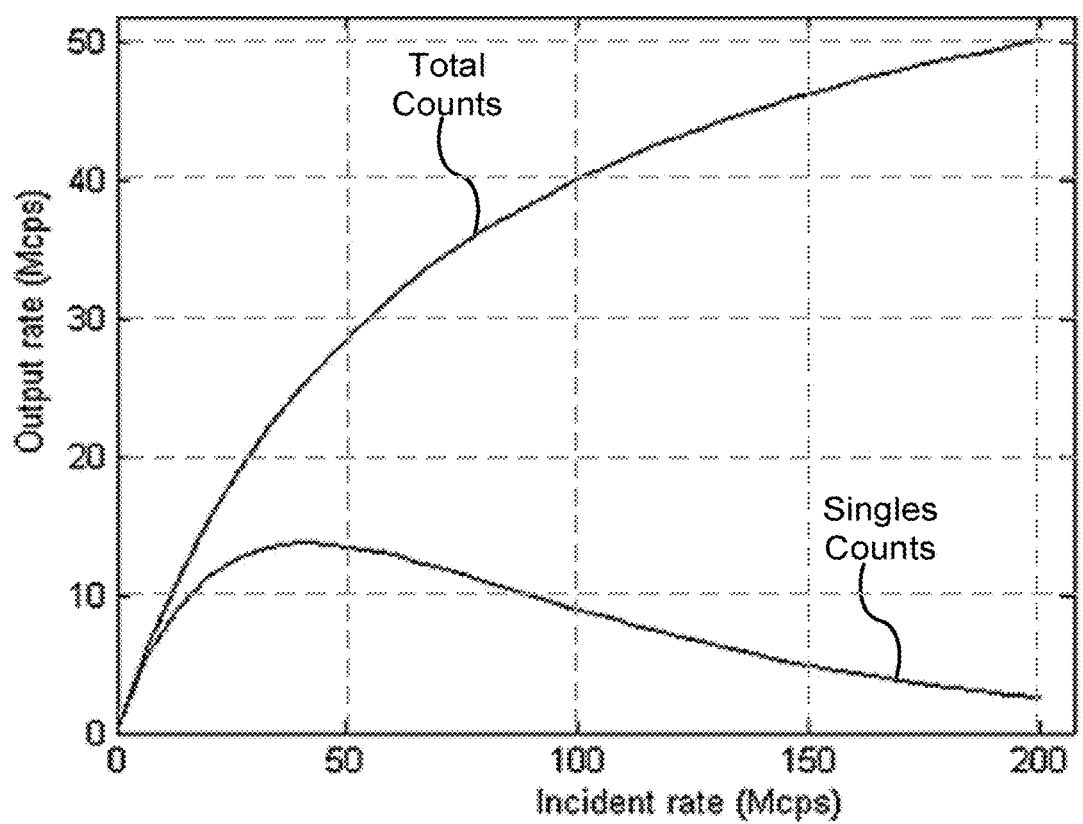
FIG. 1 shows a plot of rates of total counts and singles counts as a function of an incident flux rate.

In spectral CT, radiation having multiple energy components is used to make projective measurements of an object OBJ to generate spectrally resolved projection data. These projective measurements are made at a series of projection angles, and, using CT image reconstruction methods, images of the object OBJ can be reconstructed for each energy component (called an energy bin). However, unlike non-spectral CT, spectral CT generates additional information due to different materials exhibiting different X-ray attenuation as a function of the X-ray energy. These differences enable a decomposition of the spectrally resolved projection data into material components, usually two material components because there are two dominant attenuation mechanisms (i.e., Compton scattering and photoelectric absorption) that contribute to spectral variations in the X-ray attenuation. In clinical applications, for example, the two material components of the material decomposition can be bone and muscle, which, for imaging purposes, is predominantly composed of water. Mapping the projection data from spectral components to the material components (i.e., the material decomposition) can be performed either before or after the image reconstruction process. However, performing material decomposition prior to the reconstruction process is preferable, due to beam hardening considerations. The methods described herein can be applied either before or after image reconstruction, but only material decomposition prior to image reconstruction is expressly discussed.

When most of the X-rays have energies well above the K-edge of the majority of atoms of the imaged object OBJ, as is the case for conventional X-ray sources imaging biological objects, the material decomposition problem can be solved using only two energy components consistent with the existence of the two dominant interaction processes discussed above. Thus, spectral CT is sometimes referred to as dual-energy CT, and the material decomposition process can be referred to as dual-energy analysis. Herein, spectral CT will include at least dual-energy CT, but also includes projective measurements with more than two energy components, such that the two-material decomposition problem is overdetermined. As discussed in U.S. patent application Ser. No. 13/906,110, incorporated herein by reference in its entirety, the additional information provided by more energy bins can be used effectively in noise balancing and related methods to improve image quality.

Photon-counting detectors (PCDs) can be used to obtain spectrally resolved projection data. While PCDs have many advantageous properties, at relatively high X-ray flux such as in clinical X-ray computed tomography (CT), PCDs can exhibit nonlinear behavior due to pileup. The nonlinear PCD response can be calibrated and corrected, as discussed in U.S. patent application Ser. No. 14/676,594, incorporated herein by reference in its entirety.

A dual-energy analysis method can be used because the attenuation of X-rays in biological materials is dominated by two physical processes (i.e., photoelectric absorption and Compton scattering). Thus, the attenuation coefficient as a function of energy can be approximated by the decomposition $$\mu(E,x,y)=\mu_{PE}(E,x,y)+\mu_C(E,x,y),$$

wherein $\mu_{PE}(E,x,y)$ is the photoelectric attenuation and $\mu_C(E,x,y)$ is the Compton attenuation. Alternatively, this attenuation coefficient can be rearranged into a decomposition of a high-Z material (i.e., material 1, which can be bone) and a low-Z material (i.e., material 2, which can be water) to become $$\mu(E,x,y) \approx \mu_1(E)c_1(x,y)+\mu_2(E)c_2(x,y),$$

wherein $c_1(x,y)$ and $c_2(x,y)$ are, respectively, the first and second basis images.

A challenge of using PCDs to acquire spectrally resolved projection data is that, due to pileup, the detector response of the PCDs can be nonlinear. Correcting for pileup can be especially challenging at high X-ray fluxes such as those encountered in a clinical applications. Calibrating the PCDs and modeling the detector response of the PCDs can be used to correct for the nonlinearities of PCDs. However, these corrections will not be perfect, and these imperfections can introduce biases and errors into the material decomposition.

In contrast to using detector-response models and calibration to correct for pileup, post-selection can be used to select singles-counts projection data from the total-counts projection data. The total-counts projection data includes both single-photon and multi-photon detection events (photon here refers to X-ray photons). In contrast, the singles-counts projection data corresponds to detection events in which only a single X-ray photon arrives within the detection time window. Because the projection data corresponding to the singles counts does not require correction for pileup, the imperfections of the pileup correction do not affect the singles counts. Accordingly, a material decomposition based on the singles-counts projection data can be more precise than a material decomposition based on the total-counts projection data.

Several methods can be used to post-select singles-counts projection data from total-counts projection data. First, a pileup-rejection circuit can be incorporated into each detector to generate the singles-counts projection data at the time of detection. Second, by post-selecting the singles counts based on their unique signatures, the singles-counts projection data can be extracted from the total-counts projection data during post-processing after the projection data has been obtained. Using either method, the singles-counts projection data can be obtained.

The single-counts projection data does not need a non-linear-pileup correction and therefore a material decomposition based on the single-counts projection data can produce more accurate results than using the total-counts projection data. However, a material decomposition based on the single-counts projection data can be ambiguous because the function mapping the singles counts to incident X-ray flux on the detectors is multi-valued, whereas the same function for the total-count projection data is single valued. Thus, using the single-counts projection data for material decomposition produces multiple solutions, but once the correct solution is selected from the multiple solutions, the final result will be more precise than a similar result using multi-counts projection data. To disambiguate the material-decomposition results obtained using singles-counts projection, additional information is needed.

The methods described herein provide improved accuracy for material decomposition by combining material decomposition of the single-counts projection data together with additional information (e.g., the additional information from material decomposition based on multiple-counts projection data) to select the correct material decomposition generated using the single-counts projection data. Thus, the methods described herein achieve improved accuracy provided by using the single-counts projection data for material decomposition while overcoming the ambiguities of using the single-counts projection data.

Generally, material decomposition, whether it is performed using total-counts or single-counts projection data, can be performed using either a cost-function method or a split-step method. In the split-step method, the material-decomposition problem is subdivided into two sub-problems each corresponding to one half of the split-step method: (1) the detector-correction problem, and (2) the X-ray-absorption problem. Both of these sub-problems can be framed in terms of the projection lengths $L_1$ and $L_2$ of the material decomposition. The split-step method solves the material decomposition by iterating between the two sub-problems (i.e., steps), the latter sub-problem (step) using the results from the preceding sub-problem (step) as an input, and repeating until convergence.

The detector-correction sub-problem of the split-step method can be thought of as corresponding respectively to the detection stages of the X-ray measurements, and the X-ray-absorption sub-problem can be thought of as corresponding to the propagation/absorption stages of the X-ray measurements. The projection lengths $L_1$ and $L_2$ are given by a line integral over the coefficients $c_1(x,y)$ and $c_2(x,y)$ along the X-ray trajectory l, which can be expressed as $$L_i = \int \int_l dx dy c_i(x, y).$$

First, the X-ray-absorption problem corresponds to the change in the X-rays as the X-rays propagate from the X-ray source until they reach the PCDs. The incident X-ray flux $S(E)$ onto each detector is given by $$S(E) = n_{air} S_0(E) \exp[-\mu_1(E)L_1 - \mu_2(E)L_2],$$

wherein $n_{air}$ is the X-ray flux from the X-ray source onto the object OBJ that is being imaged, $L_1$ and $L_2$ are projection lengths given by the line integrals along the X-ray trajectory and correspond respectively to the first and second material of the material decomposition, and $S_0(E)$ is a normalized spectrum of the incident X-ray flux as a function of energy E (e.g., $\int dE\, S_0(E)=1$).

Second, the detector-correction problem corresponds to a mapping from the incident X-ray flux on the PCDs to the measured counts on the PCDs. The mapping from the incident flux on the PCDs to the measured counts can be nonlinear and depend on the incident flux $S(E)$ on the PCDs. Thus, the detector-correction problem depends on the projection lengths $L_1$ and $L_2$ because the detector-correction problem depends on the incident flux $S(E)$.

Accordingly, the detector-correction problem uses the incident flux $S(E)$, which includes the information of the projection lengths $L_1$ and $L_2$, to calculate corrected projection data. Relatedly, the X-ray-absorption problem uses the corrected projection data from the detector-correction problem to calculate the projection lengths $L_1$ and $L_2$ generating the incident flux $S(E)$. Thus, each sub-problem incorporates as an input the output generated by the other sub-problem.

The split-step method is performed by alternating between using the projection lengths $L_1$ and $L_2$ to update the corrected projection data and then using the updated corrected projection data to update the projection lengths $L_1$ and $L_2$, which then are used to update the corrected projection data, and so forth until convergence. After iterating between these two steps multiple times, the projection lengths $L_1$ and $L_2$ converge and the result is output as the material decomposition. Details of the split-step method are provided in U.S. patent application Ser. No. 14/593,818, incorporated herein by reference in its entirety, wherein the split-step method is referred to as the iterative method.

An alternative to the split-step method is the cost-function method, which also performs the material decomposition. In the cost-function method, a pair of projections lengths $L_1$ and $L_2$ is used to calculate model projection data, and the model projection data is compared to the actual projection data using a cost function. Smaller values of the cost function correspond to closer agreement between the actual projection data and the model projection data. optimization can be used to find the pair of projections lengths $L_1$ and $L_2$ that minimize the cost function, and this pair of projection lengths are the material decomposition. The model projection data is calculated using a model that includes both the absorption arising from transmission through the object OBJ and a detector-response model of the PCDs. Thus, the two sub-problems of the split-step method are simultaneously solved by minimizing the cost-function method. Details of the cost-function method are provided in U.S. patent application Ser. No. 14/603,135, incorporated herein by reference in its entirety. Further, U.S. patent application Ser. No. 14/674,594, incorporated herein by reference in its entirety, provides additional details regarding the detector-response model used in the material decomposition methods described herein.

In summary, if a material decomposition is performed using single-counts projection data, the material decomposition will generally be ambiguous because multiple possible solutions will be generated. For example, if a cost function is used, the cost function will have multiple local minima. In certain implementations and in the absence of noise, the correct pair of projection lengths for the material decomposition can be determined by finding a global minimum of the cost function. However, in the presence of noise, additional information is used to determine which local minimum corresponds to the correct material decomposition.

Referring now to the drawings, wherein like reference numerals designate identical or corresponding parts throughout the several views, FIG. 1 shows a plot of the output rate (e.g., measured counts $N'_m$) as a function of the incident rate (e.g., the incident X-ray flux n) for a PCD. The "Total Counts" curve indicates the number of counts $N'_m$ including both detection events in which only a single photon arrives at a PCD within the detection window and multiple-photon counts in which more than one photon arrives at a PCD within the detection window (e.g., pileup counts). The "Singles Counts" curve indicates the number of counts $N'^{(single)}_m$ including only single-photon counts (i.e., excluding pileup counts). Both curves are approximately linear near-zero flux and fall below the linear count rate as the X-ray flux increases. However, within the bounds of FIG. 1, the total counts continue to monotonically increase as a function of the flux, whereas the singles counts rolls over and begins to decrease for incident flux rates exceeding approximately 40 Mcps.

Accordingly, the multivalued nature of the "Singles Counts" makes ambiguous the incident flux and by extension the attenuation of X-rays traversing the object OBJ. That is, each value of the "Singles Counts" corresponds to two different incident fluxes. For example, a singles counts output of 10 Mcps corresponds to both an input X-ray flux of approximately 20 Mcps and an input X-ray flux of approximately 90 Mcps. In certain situations, a priori information may enable disambiguating a particular measurement. For example, if the incident X-ray flux could not exceed 80 Mcps, then a singles counts output of 10 Mcps will uniquely correspond to an incident flux of 20 Mcps because 90 Mcps would not be a physically realistic result. However, there are also situations in which a priori information does not enable a unique choice of incident flux based on FIG. 1. In these cases the additional information discussed above is used to disambiguate a material decomposition based on the singles-counts projection data.

Figure 2:
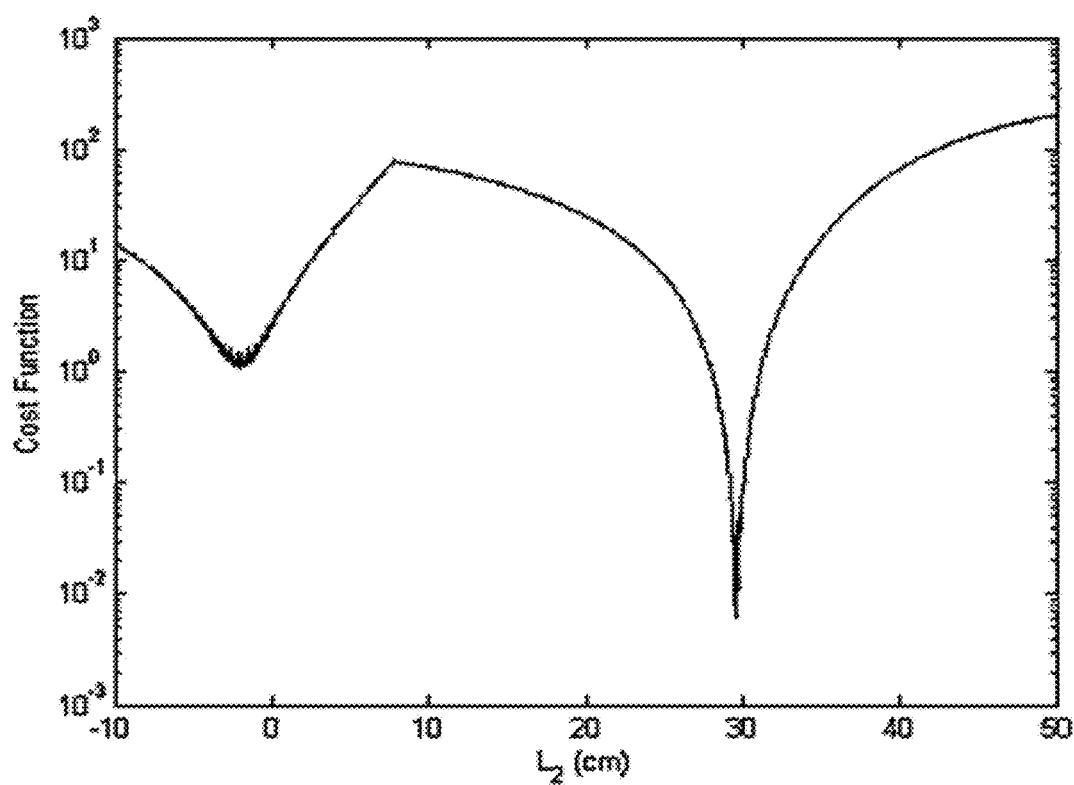
FIG. 2 show a plot of a cost function as a function of a second projection length $L_2$ when a first projection length $L_1$ is held constant.

FIG. 2 shows a plot of a cost function $\varphi(L_1, L_2)$ using the single counts projection data. In FIG. 2, the cost function $\varphi(L_1, L_2)$ is shown with the projection length $L_1$ held constant and the projection length $L_2$ allowed to vary. The cost function $\varphi(L_1, L_2)$ has two local minima each corresponding to a different value of the projection length $L_2$. Either of these two local minima might correspond to the correct material decomposition. In the absence of noise, the global minimum of the no-pileup cost-function $\varphi(L_1, L_2)$ corresponds to the correct material decomposition. However, in the presence of noise, the correct material decomposition cannot be distinguished by determining which local minimum has the smallest value.

As stated above, additional information can be used to disambiguate the correct singles-counts material decomposition. Four methods of unambiguous singles-counts material decomposition are discussed herein. The first three methods include directly solving the singles-counts material decomposition problem. These three methods also use the total-counts projection data in various ways to provide the additional information used to select the correct material decomposition from among the multiple solutions generated using the singles-counts projection data. The fourth method combines the singles-counts projection data with energy-integrated projection data to use a combined cost function method to generate a unique and precise material decomposition.

1) Method #1: Limit the Search Region for Singles-Counts Material Decomposition to a Neighborhood Surrounding the Total-Counts Material Decomposition.

In one implementation, a material decomposition is performed using the total-counts projection data to obtain a total-counts projection-length pair. Although, the correct singles-counts projection-length pair can differ from the total-counts projection-length pair, the total-counts projection-length pair can be much closer to the correct singles-counts projection-length pair than to the incorrect singles-counts projection-length pair. Thus, by defining an appropriately sized search region around the total-counts projection-length pair, the correct singles-counts projection-length pair will be included within the search region and the incorrect singles-counts projection-length pair will be excluded from the search region. Thus, constraining the solution of the singles-counts material decomposition problem to the search region forces the singles-counts material decomposition problem to converge to the correct singles-counts projection-length pair. Accordingly, after defining the search region, the singles-counts material-decomposition problem is solved subject to the constraint of the search region.

2) Method #2: Obtain All Singles-Counts Projection-Length Pairs and the Total-Counts Projection-Length Pair, and Select, as the Material Decomposition, the Singles-Counts Projection-Length Pair Closest to the Total-Counts Projection-Length Pair.

In another implementation, the total-counts projection-length pair and the singles-counts projection-length pairs are obtained. To determine which of the singles-counts projection-length pairs is the correct material decomposition, a difference is calculated between each singles-counts projection-length pair and the total-counts projection-length pair. The correct singles-counts projection-length pair is the singles-counts projection-length pair closest to the total-counts projection-length pair.

3) Method #3: Obtain All Singles-Counts Projection-Length, Determine the Total-Counts Cost Function Value for Each Singles-Counts Projection-Length Pair, and Select, as the Material Decomposition, the Singles-Counts Projection-Length Pair Corresponding to the Smallest Value of the Total-Counts Cost Function.

In another implementation, the singles-counts projection-length pairs are obtained and used to calculate cost-function values using the total-counts cost function. The pair of projection lengths corresponding to the lowest value of the total-counts cost function is then selected as the material decomposition. The total-counts cost function can be used to disambiguate the singles-counts projection-length pairs because the correct singles-counts projection-length pair will be closer to the minimum of the total-counts cost function than would be an incorrect singles-counts projection-length pair.

4) Method #4: Minimize a Combined Cost Function to Find a Global Minimum; the Combined Cost Function Combines Results Obtained Using the Singles-Counts Projection Data and Projection Data from Energy-Integrating Detectors.

In a fourth implementation, a combined cost function is used to uniquely determine the material decomposition. The combined cost function combines, for a given projection-length pair, the distance between the measured singles-counts projection data and a modeled singles-counts value and the distance between projection data obtained using an energy-integrating detector and a modeled energy-integrating value. Energy-integrating detectors do not suffer from the same pileup effects as do the PCDs. Thus, energy-integrating detectors can be used together with the singles-counts projection data to provide additional information to generate the correct material decomposition. Further, the energy-integrating projection data can be used together with the single-counts projection data without introducing biases or errors because the projection data from the energy-integrating detector does not suffer from pileup and imperfect pileup corrections. Incorporating the energy-integrating projection data with the single-counts projection data into a combined cost function removes the ambiguity of a cost function relying exclusively on the single-counts projection data. Accordingly, the global minimum of the combined cost function yields the correct material decomposition.

The details of each of these methods of unambiguously performing material decomposition using the single-counts projection data are described below.

Figure 3:
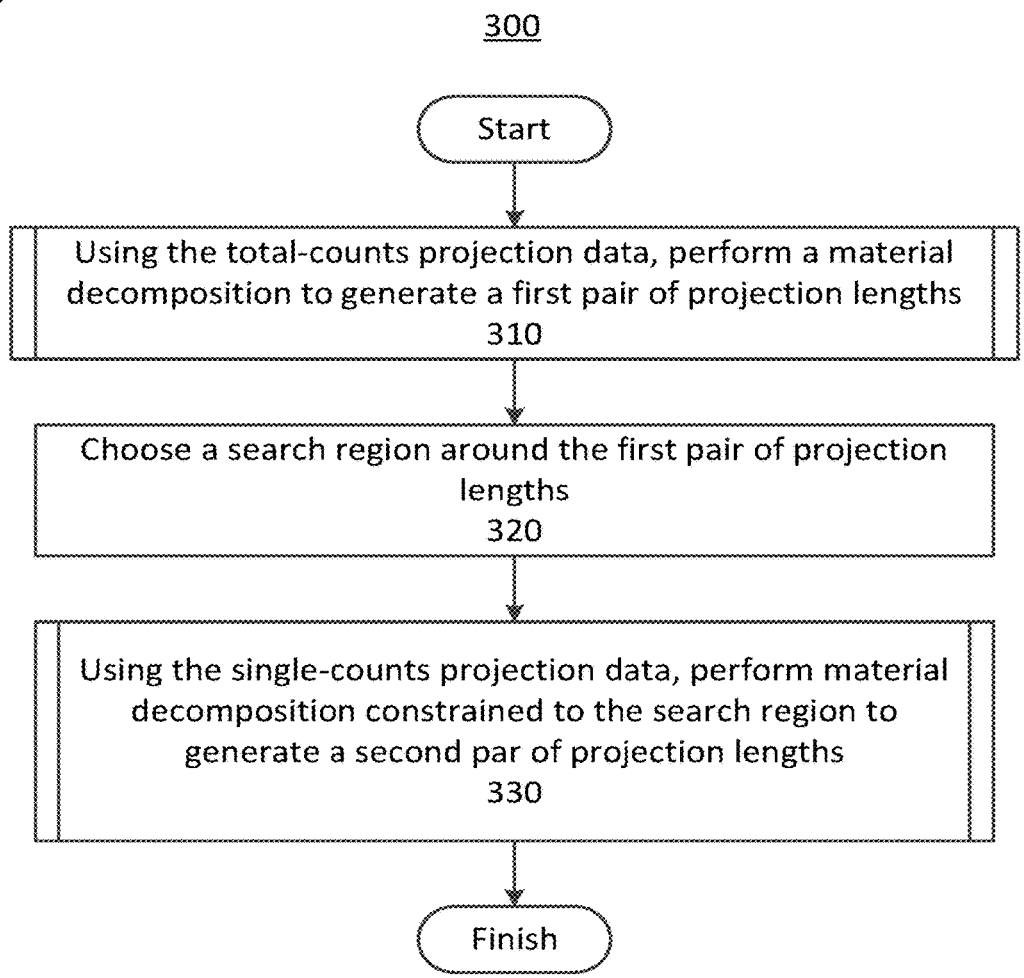
FIG. 3 shows a flow diagram of an implementation of a constrained search-region method for material decomposition.

FIG. 3 shows a flow diagram of a constrained search-region method 300 of performing material decomposition using singles-counts projection data and total-counts projection data.

In process 310 of method 300, a total-counts projection-length pair $L_1^{(T)}$ and $L_2^{(T)}$ is obtained. For example, this total-counts projection-length pair $L_1^{(T)}$ and $L_2^{(T)}$ can be determined by using optimization to minimize the total-counts cost function or by iteratively performing the split-step method described above.

In step 320 of method 300, a search region SR is defined, according to predefined criteria, to surround the total-counts projection-length pair $L_1^{(T)}$ and $L_2^{(T)}$, according to predefined criteria. The predefined criteria are selected in order that the search region SR includes the correct singles-counts projection-length pair while excluding the incorrect singles-counts projection-length pair. For example, the predefined criteria can be based on empirical results obtained from experiments to determine how large to make the search region SR.

In process 330 of method 300, a singles-counts projection-length pair is obtained by performing material decomposition subject to the constraint of the search region SR and using the singles-counts projection data. For example, the material decomposition can be performed using constrained optimization to minimize the singles-counts cost function.

Alternatively, the material decomposition can be performed by iteratively solving the split-step method starting from an initial value of the total-counts projection-length pair $L_1^{(T)}$ and $L_2^{(T)}$, and constrained to maintain the projection-length pairs within the search region SR.

Figure 4:
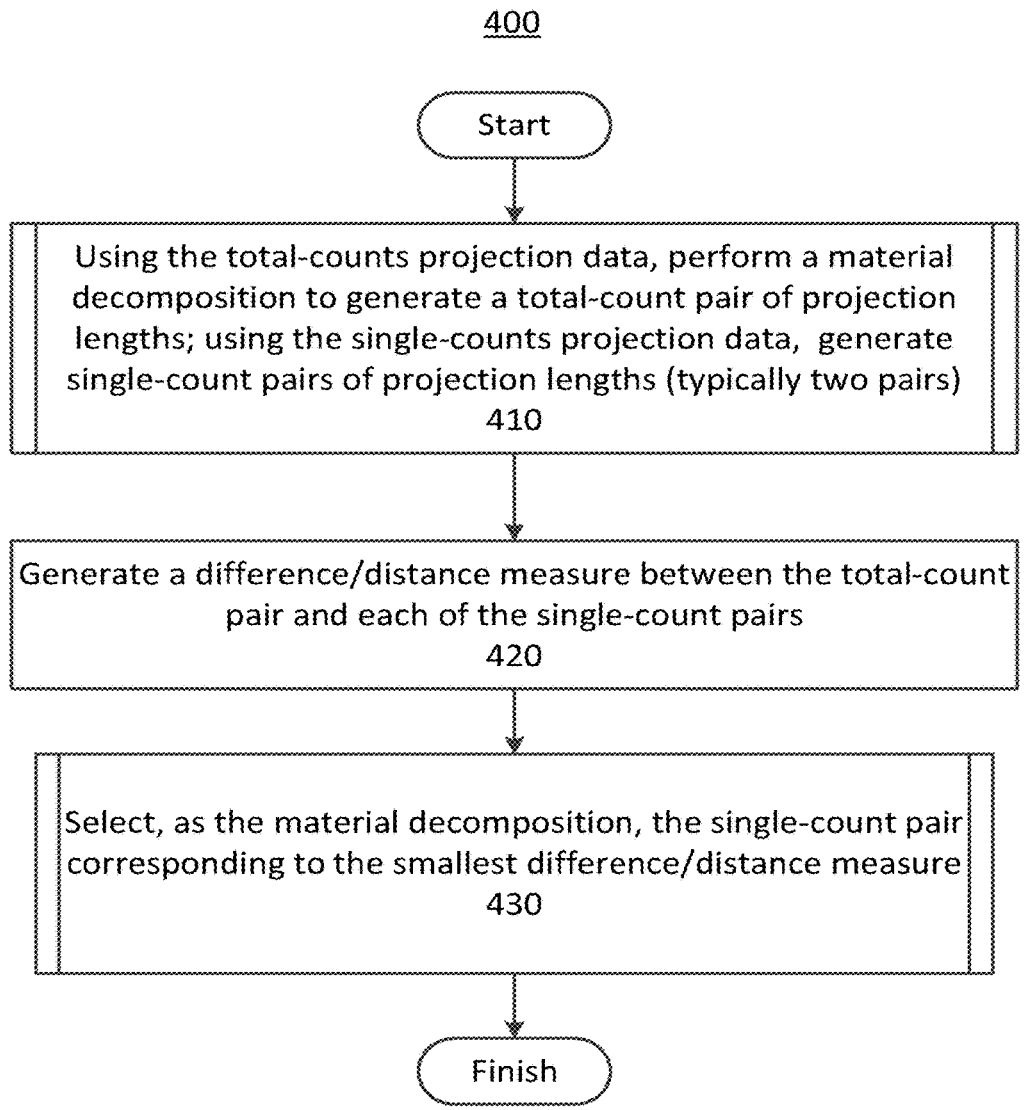
FIG. 4 shows a flow diagram of an implementation of a difference-comparison method for material decomposition.

FIG. 4 shows a flow diagram of a difference-comparison method 400 of performing material decomposition using singles-counts projection data and total-counts projection data.

In process 410 of method 400, a total-counts projection-length pair $L_1^{(T)}$ and $L_2^{(T)}$ is obtained. For example, this total-counts projection-length pair $L_1^{(T)}$ and $L_2^{(T)}$ can be determined by using optimization to minimize the total-counts cost function or by iteratively performing the split-step method described above.

Also, singles-counts projection-length pairs $L_{1,i}^{(S)}$ and $L_{2,i}^{(S)}$ are obtained, wherein i is an index of the projection-length pairs. Whereas the total-counts material decomposition problem only generates a single projection-length pair (e.g., the total-counts cost function only has a single local minimum which can be found using optimization), the singles-counts material decomposition problem generally generates two projection-length pairs (e.g., the singles-counts cost function can have two local minima which can be found using optimization). The first projection-length pair can be found using either of the cost-function or split-step methods and starting from any initial value. The trajectory of the search for the first projection-length pair is used to define an exclusion region for subsequent searches. Then a second initial value can be selected to search for second local minimum. The second initial value is selected to be outside the exclusion region that surrounds the trajectory of the first search. If the second search converges to the first local minimum, then the exclusion region is expanded to include a region surrounding the second search trajectory and another initial value is selected outside of the exclusion region and another search is performed. This process is repeated until a second local minimum is found. Thus, two different projection length pairs are obtained corresponding to solutions of the singles-counts material decomposition problem.

In step 420 of method 400, respective differences/distances are determined between the total-counts projection length pair and each of the singles-counts projection length pairs. For example, the difference/distance measure can be a Euclidian distance.

In process 430 of method 400, the singles-counts projection length pair that is closest to the total-counts projection length pair, as determined by the difference/distance measure used in step 420, is selected as the correct material decomposition.

Figure 5:
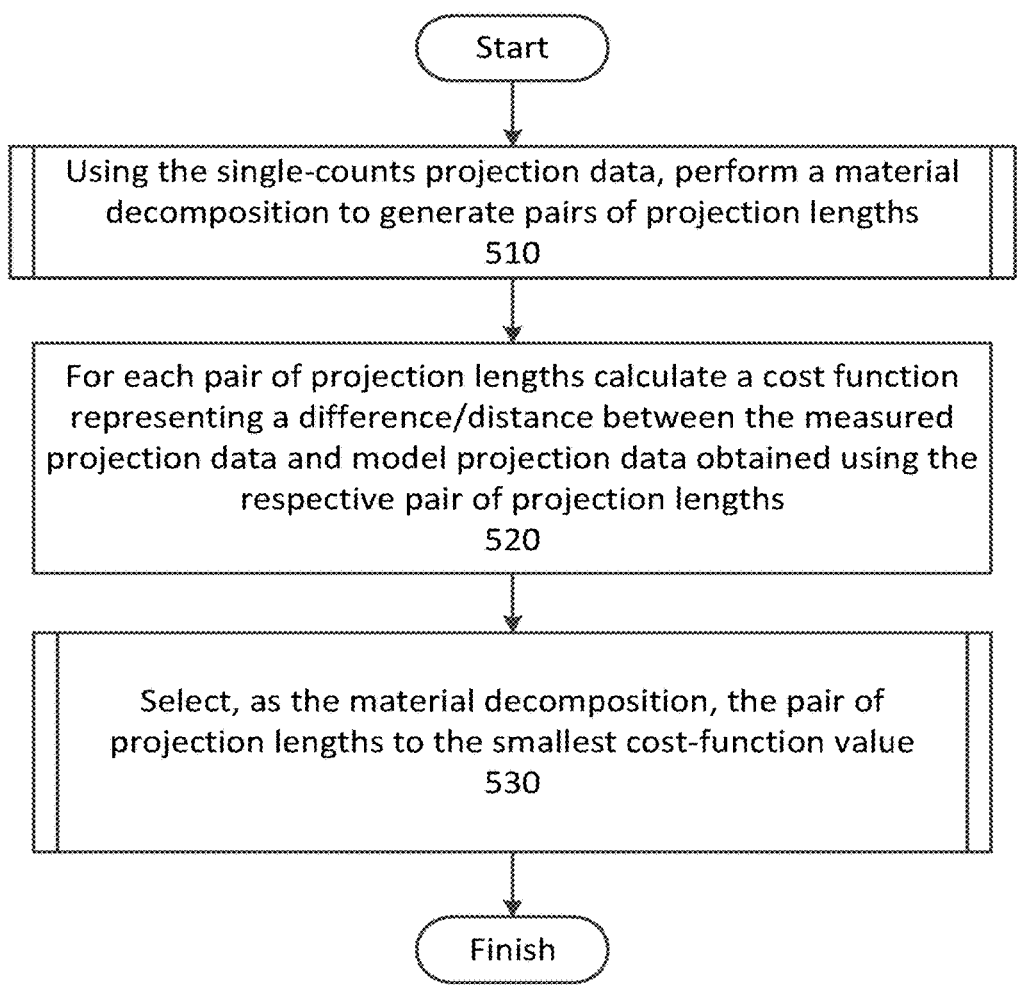
FIG. 5 shows a flow diagram of an implementation of a cost-function-comparison method for material decomposition.

FIG. 5 shows a flow diagram of a cost-function-comparison method 500 of performing material decomposition using singles-counts projection data and total-counts projection data.

In process 510 of method 500, singles-counts projection-length pairs are obtained. For example, singles-counts projection-length pairs can be obtained using any of the methods discussed for process 410 of method 400.

In step 520 of method 500, respective cost-function values care calculated corresponding to each of the singles-counts projection-length pairs. The cost-function values are calculated by using the total-counts cost function.

In process 530 of method 500, the singles-counts projection-length pair corresponding to the lowest cost-function value is selected as the material decomposition.

Figure 6:
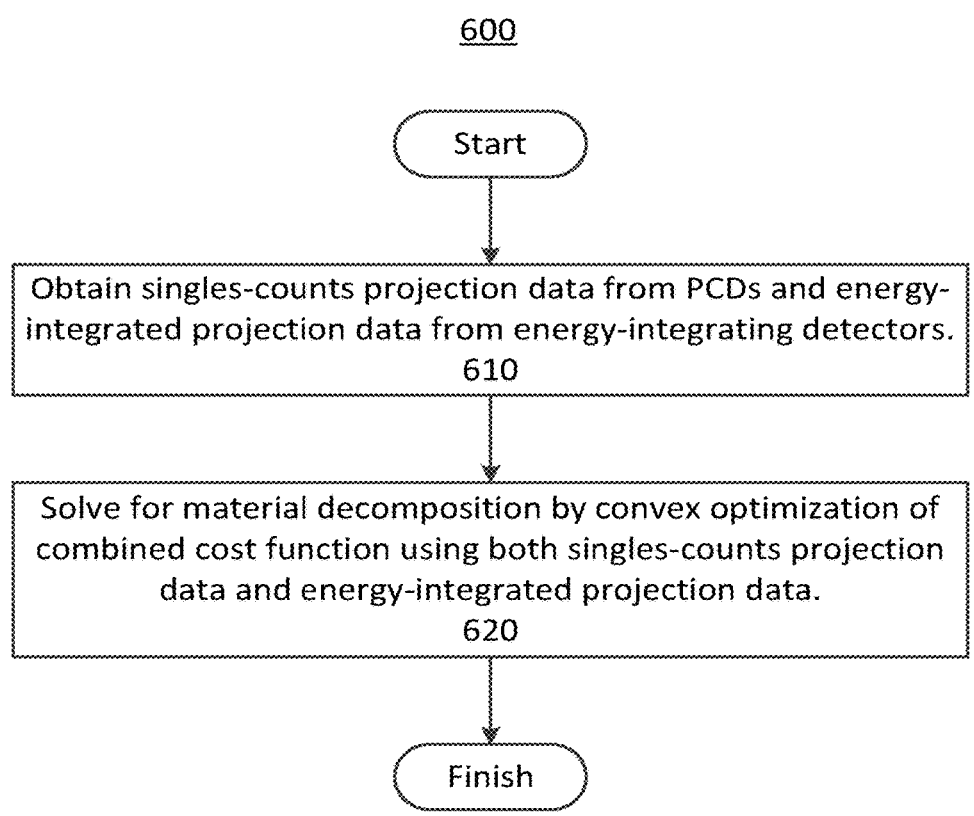
FIG. 6 shows a flow diagram of an implementation of a combined cost-function method for material decomposition.

FIG. 6 shows a flow diagram of a combined-cost-function method 600 of performing material decomposition using singles-counts projection data and energy-integrated projection data.

In step 610 of method 600, singles-counts projection data from the PCDs and energy-integrated projection data from an energy-integrating detector are obtained. Energy-integrating detectors such as scintillation elements with photomultiplier tubes (PMTs) or avalanche photo-diodes (APDs) can convert a single high-energy X-ray photon into multiple lower-energy optical photons called scintillation photons. Then the resultant scintillation photons are detected using the optical detectors (e.g., the PMTs and/or APDs). This type of detection is not susceptible to pileup and the nonlinear detector response of the PCDs either. Accordingly, the energy-integrated projection data can be used to disambiguate the material decomposition of the singles-counts projection data without introducing the biases and errors native to the total-counts projection data.

In step 620 of method 600, material decomposition is performed by optimization of a combined singles-counts and energy-integrated cost function. For example, the combined cost function can be given by $$\phi(L_1, L_2) = \frac{\left(V_i^{(meas.)} - V_i^{(model)}(L_1, L_2)\right)^2}{\text{var}(V_i^{(meas.)})} + \lambda \sum_{i=1}^{n_{bins}} \frac{\left(N_i^{(meas.)} - N_i^{(model)}(L_1, L_2)\right)^2}{N_i^{(meas.)}} L_1$$

wherein $\varphi(L_1, L_2)$ is the combined cost function, $N_i^{(meas.)}$ the number of singles counts measured for the $i^{th}$ energy bin, $N_i^{(model)}(L_1, L_2)$ is the number of singles counts for a model of the $i^{th}$ energy bin when the projection-length pair is given by $L_1$ and $L_2$, $n_{bins}$ is the total number of energy bins, $\lambda$ is a weighting factor to adjust the relative influence between the singles-counts projection data and energy-integrated projection data, $V_i^{(meas.)}$ is the measured energy-integrated projection data, $V_i^{(model)}(L_1, L_2)$ is the model value of the energy-integrated projection data when the projection-length pair is $L_1$ and $L_2$ and var($V_i^{(meas.)}$) is the variance of the measured energy-integrated projection data. Other distance measures and combinations of the singles-counts and energy-integrated projection data can also be used. The material decomposition problem can be solved by finding the projection-length pair that minimizes the combined singles-counts and energy-integrated cost function.

Figure 7A:
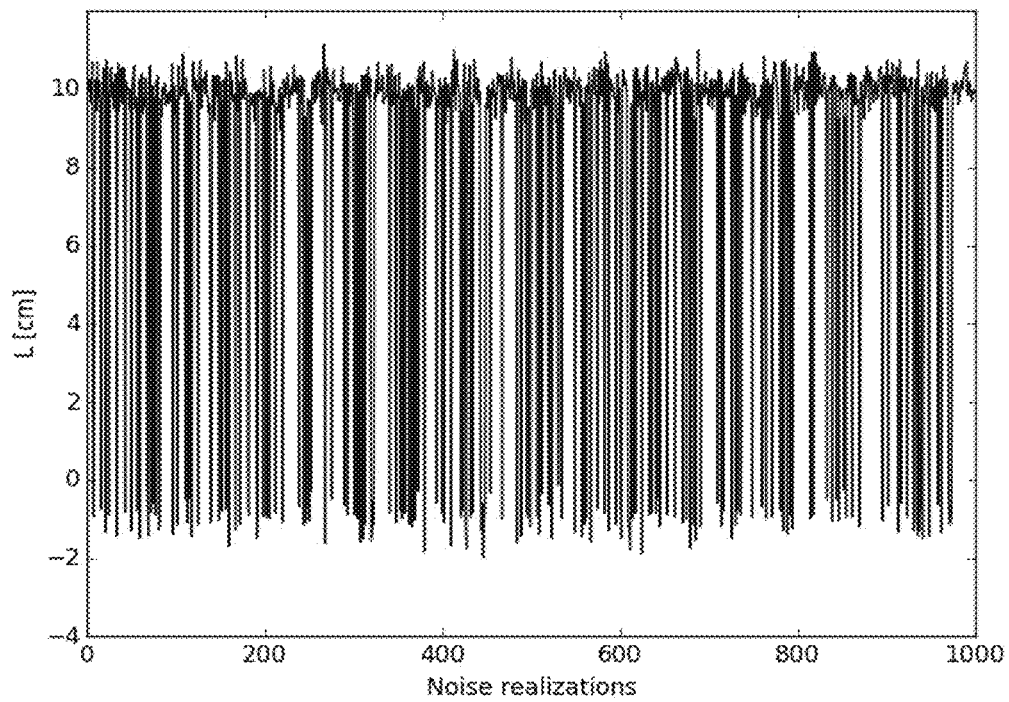
FIG. 7A shows a plot of 1000 simulations of a material decomposition using the singles-count projection data only, the noise is different for each simulation.

FIG. 7A shows a plot of a projection length generated by 1000 iterations of material decomposition experiment. In each iteration, a different noise realization is combined with the singles-counts projection data, and material decomposition is performed on the combination of signal and noise. The material decomposition is performed on the combination of signal and noise to generate a maximum likelihood estimate the projection lengths, which estimates are shown in FIG. 7A. FIG. 7A plots the estimate of the first projection length $L_1$ as a function of the noise realization. Clearly, many of these estimates resulted in the wrong projection length—the correct value is approximately 10 cm.

Figure 7B:
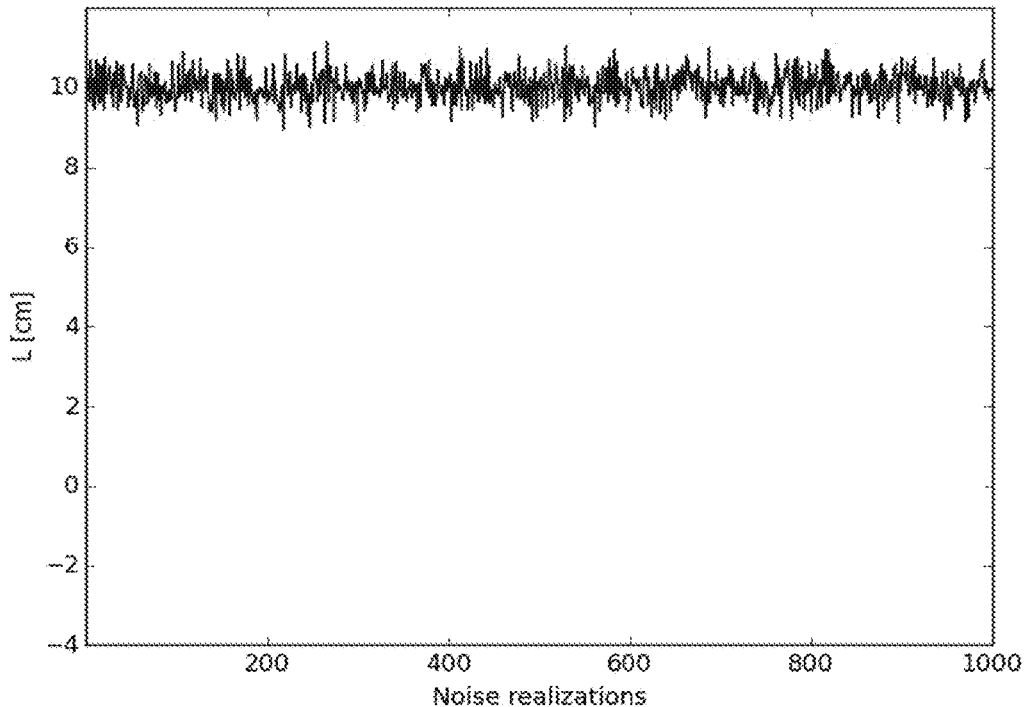
FIG. 7B shows a plot of 1000 simulations of a material decomposition using a combined cost function including both singles-count projection data and energy-integrated projection data, the noise is different for each simulation.

FIG. 7B shows a plot of the result of 1000 experiments using the same noisy signals as in FIG. 7A, but the combined cost function including both the singles-counts projection data and the energy integrated projection data was used, rather than using only the singles-counts projection data. Using the combined cost function, the estimate of the projection length consistently generates a value approximating the correct value for the first projection length $L_1$ for all 1000 experiments.

Next, a detector model of semiconductor-based PCDs is discussed. This model variously applies to both the cost-function method and the split-step method.

As discussed in U.S. patent application Ser. No. 13/866,965, incorporated herein by reference in its entirety, the response function of the radiation detectors can be calibrated to provide improved results. In one implementation, the detector model for the number of counts of each given radiation detector is $$N_m = Tne^{-n\tau}\iint dEdE_0 R_0(E,E_0)S(E_0) + T n^2 e^{-n\tau}\iiint dEdE_0 dE_1 R_1(E,E_0,E_1)S(E_0)S(E_1),$$

wherein each of the integrating time T, linear response function $R_0$, nonlinear response function $R_1$, and dead time $\tau$ are known for each radiation detector and energy component as a result of calibrations performed before the projective measurements on object OBJ. In the above nonlinear detector model, only the first order nonlinear term is included. Generally, higher order nonlinear terms can also be included in the detector model for the number of counts. Each integral is integrated over the spectral range for the $m^{th}$ energy bin. Thus, there is a unique count $N_m$ for each energy bin/component of each detector.

The detected spectrum is given by $$S(E_i) = S_{air}(E_i)\exp[-\mu_1(E_i)L_1 - \mu_2(E_i)L_2],$$

wherein the attenuation coefficients $\mu_1$ and $\mu_2$ are known functions of the X-ray energy, and the spectrum in the absence of an object OBJ (designated by $S_{air}$) is also known.

Similarly, the X-ray flux n for each detector is given by $$n = n_{air}\int dE_0 S(E_0)\exp[-\mu_1(E_0)L_1 - \mu_2(E_0)L_2],$$

wherein $n_{air}$ is known. In one implementation, which is discussed more completely in U.S. patent application Ser. No. 14/103,137, incorporated herein by reference in its entirety, the value of $n_{air}$ is given by $$n_{air} = A \cdot I_{ref},$$

wherein A is a calibration term unique to each detector that is determined before the projective measurements on object OBJ, and $I_{ref}$ is the reference detector signal.

The projection lengths $L_1$ and $L_2$ can be calculated by minimizing a cost function $\varphi(L_1, L_2)$ that compares the measured counts of the PCDs $N'_m = N_m^{(meas.)}$ with the calculated counts $N_m = N_m^{(model)}$ using a detector response model, such as the model discussed above. The same nomenclature is used for both the total-counts projection data and the singles-counts projection data, and in each case the correct interpretation of the nomenclature is evident to a person of ordinary skill in the art based on context. The model for the singles-counts projection data is the same as the total-counts projection data absent the higher order terms.

Several different definitions of the cost function $\varphi(L_1, L_2)$ can be used represent a difference measure between the measured counts $N'_m$ and the modeled counts $N_m$. In one implementation, the cost function is the least squares of the difference between the measured counts $N'_m$ and the modeled counts $N_m$, i.e., $$\varphi_{Pileup}(L_1,L_2) = \Sigma(N'_m - N_m)^2.$$

In one implementation, the cost function is the weighted least squares of the difference between the measured counts $N'_m$ and modeled counts $N_m$, i.e., $$\varphi_{Pileup}(L_1, L_2) = \sum \frac{(N'_m - N_m)^2}{\sigma_m^2},$$

wherein $\sigma_m$ is the standard deviation of $N'_m$.

In one implementation, the cost function is the Poisson likelihood function, i.e., $$\varphi_{pileup}(L_1,L_2) = \Sigma[N'_m \log(N_m) - N_m].$$

The cost-function material decomposition method can be performed by using any optimization method to solve $$\arg\min_{L_1,L_2}\{\phi\}$$

in order to obtain a pair of projection lengths. If the material decomposition is constrained to a search region than a constrained optimization method can be used.

To find these local minima, any local optimization method can be used. For example, the local minima can be obtained to using any local optimization method, including: a Nelder-Mead simplex method, a gradient-descent method, a Newton's method, a conjugate gradient method, a shooting method, or other known local optimization methods.

When the cost function has more than one local minima, a robust stochastic optimization process is beneficial to find the global minimum and all of the local minima of the cost function. There are many known methods for finding global minima including: genetic algorithms, simulated annealing, exhaustive searches, interval methods, and other deterministic, stochastic, heuristic, and metaheuristic methods.

Figure 8:
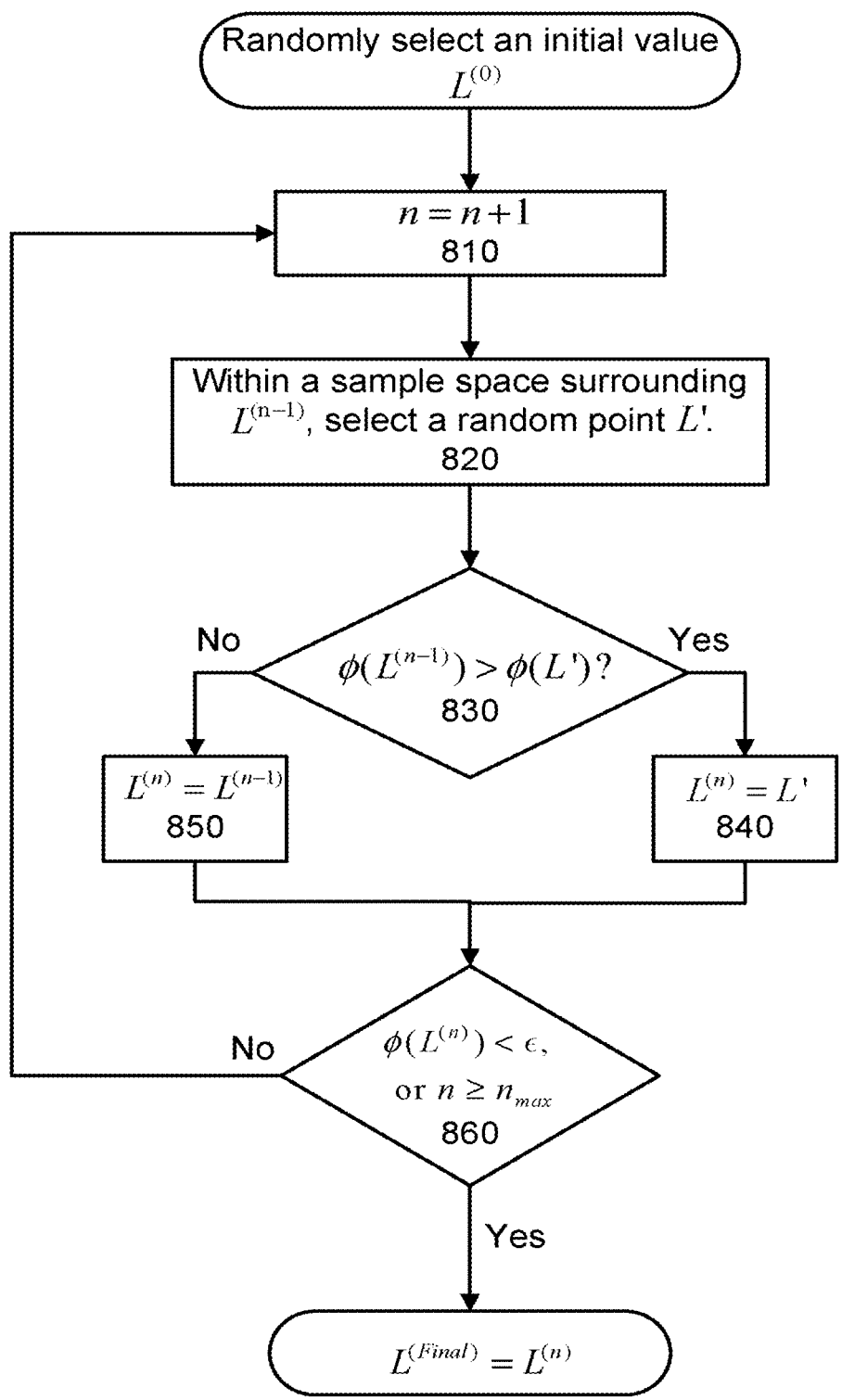
FIG. 8 shows a flow diagram of an implementation of a cost-function method to perform material decomposition.

In one implementation, the method 800 shown in FIG. 8 can be used to find a minimum of a cost function. Method 800 starts when a random value is selected as the initial guess for $L^{(0)} = (L_1^{(0)}, L_2^{(0)})$. Next, at step 810 the loop variable n is incremented.

Following step 810, the method 800 proceeds to step 820, wherein a new sample point L' is randomly selected from the sample space surrounding the current set of projection lengths $L^{(n-1)} = (L_1^{(n-1)}, L_2^{(n-1)})$.

Proceeding to step 830, the method 800 inquiries as to which of value of the cost function $\varphi(L^{(n-1)})$ or $\varphi(L')$ is smaller. In steps 840 and 850 the argument corresponding to the smaller value of the cost function is assigned as the next set of projection lengths $L^{(n)} = (L_1^{(n)}, L_2^{(n)})$ for the next loop iteration.

Step 860 of method 800 evaluates whether the loop stopping criteria is satisfied. Although different stopping criteria can used, FIG. 8 shows an implementation wherein the loop stops when either a maximum number of loop iterations $n_{max}$ has been reached or the cost function falls below a predetermined threshold $\epsilon$. If the stopping criteria are satisfied, the method 800 exits the loop at 860 and reports the current projection length $L^{(n)} = (L_1^{(n)}, L_2^{(n)})$ as the final projection length. Otherwise, the loop continues by proceeding from step 860 back to step 810.

In addition to the cost-function method discussed above, a split-step method of performing the material decomposition is discussed in U.S. patent application Ser. No. 14/593,818, incorporated herein by reference in its entirety. This split-step method solves the material decomposition problem by alternating between using projection length estimates to correct the measured counts for the nonlinear response of the PCDs and then using the corrected counts to generate new projection length estimates.

Figure 9:
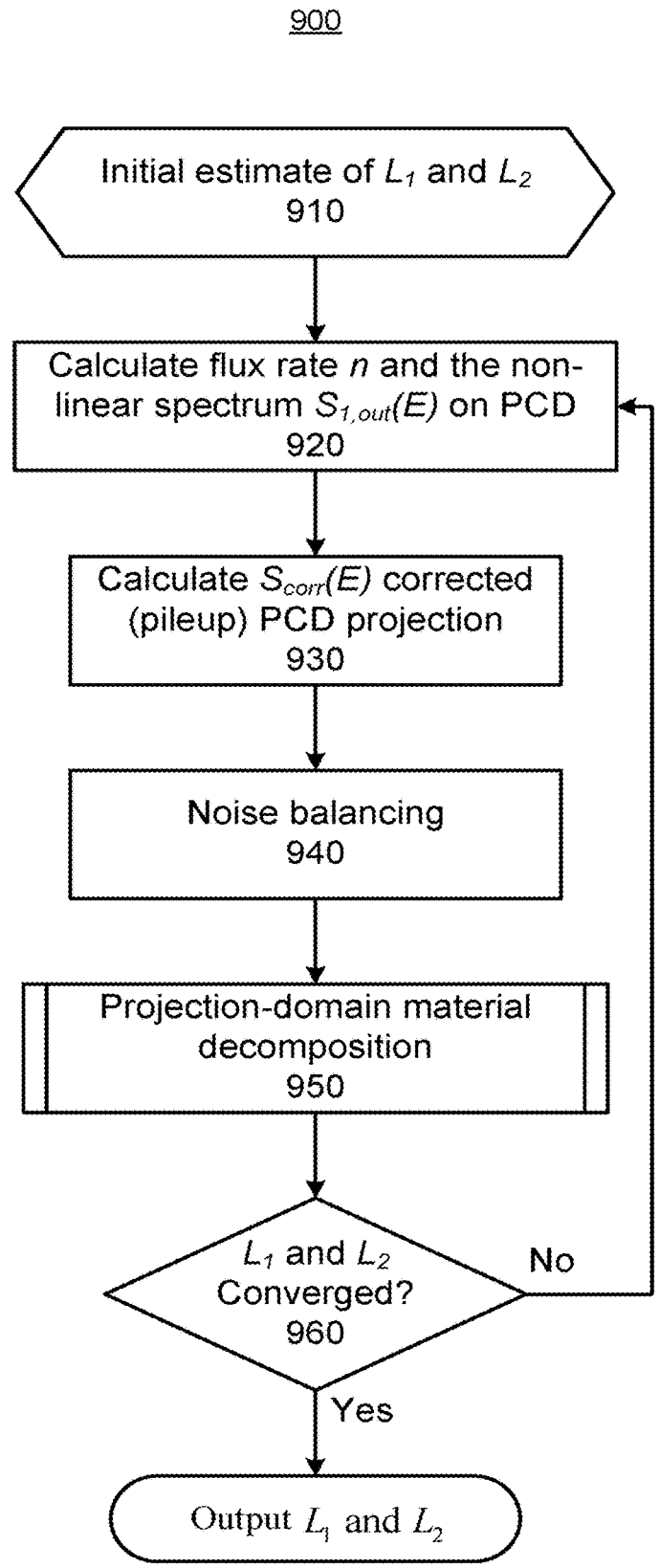
FIG. 9 shows a flow diagram of an implementation of a split-step method to perform material decomposition.

FIG. 9 shows one implementation of the split-step method 900. In FIG. 9, a split-step method 900 for solving the material decomposition problem is exemplified for the case of total-counts projection data. This method solves for the projection lengths $L^{Final}=(L_1, L_2)$.

As shown in FIG. 9, method 900 begins when an initial estimate of the projection lengths $L_1$ and $L_2$ are input into the first step 920 of an iterative loop. After the first iteration of the large loop including steps 920 through 960, the projection lengths $L_1$ and $L_2$ are fed back from material decomposition in process 950 to the first step 920 of the large iterative loop. In contrast to subsequent loop iterations using projection lengths calculated by the material decomposition in process 950, the first iteration uses the initial estimate of the projection lengths from step 910.

Receiving the projection length estimates, the large loop begins at step 920 by calculating the X-ray flux rate $$n = n_{air} \int dE_0 S_{air}(E_0) \exp[-\mu_1(E_0)L_1 - \mu_2(E_0)L_2],$$

and the nonlinear spectrum term $S_{Nonlin.}(E)$ discussed previously. In the implementation shown in FIG. 9, the nonlinear spectrum includes only the first order pileup, which is given by $$S_{1,out}(E) = \iint dE_0 dE_1 R_1(E, E_0, E_1) S_{in}(E_0) S_{in}(E_1),$$

wherein $$S_{in}(E) = S_{air}(E) \exp[-\mu_1(E)L_1 - \mu_2(E)L_2].$$

Next at step 830 of method 800, the corrected detector spectrum is calculated to correct for pileup as given by $$S_{Corr.}(E) = S_{Raw}(E) - S_{Nonlin.}(E),$$

wherein $S_{Raw}(E)$ is the raw measured spectrum before detector response corrections. The corrected energy count is given by $$N_m^{Corr.} = T \int dE W_m(E) S_{Corr.}(E),$$

wherein T is the integration time. For the singles-counts projection data the higher order corrections associated with pileup can be omitted.

In one implementation, the corrected count of the $m^{th}$ energy bin of the PCD is given by $$N_m^{Corr.} = N_m^{Raw} - N_m^{Nonlin.}$$

wherein $N_m^{Corr.}$ is the corrected count value of the $m^{th}$ energy bin of the PCD, $N_m^{Raw}$ is the raw count value recorded from the detector, and $N_m^{Nonlin.}$ is the calculated count from the nonlinear detector response. The nonlinear count value $N_m^{Nonlin.}$ is calculated according to $$N_m^{Nonlin.} = T \int dE w_m(E) S_{Nonlin.}(E).$$

In some implementations, the nonlinear spectrum correction includes only the first order pileup; while in other implementations, the nonlinear spectrum correction includes higher-order pileup terms. For example, higher order terms can be omitted for singles-counts projection data.

The method 900 then proceeds to step 940. In step 940, noise balancing is performed by dividing the detector counts into high- and low-energy components in preparation for material decomposition. The noise-balancing process of apportioning the counts into high- and low-energy components is described in U.S. patent application Ser. No. 13/906,110, incorporated herein by reference in its entirety. The noise balancing in step 940 results in partitioning the counts from the energy bins into high- and low-energy components according to $$N_H = \sum_m a_m^{(H)} N_m^{Corr.}, \text{ and}$$

$$N_L = \sum_m a_m^{(L)} N_m^{Corr.},$$

wherein $\sum_m \alpha_m^{(H)} = 1$, $\sum_m \alpha_m^{(L)} = 1$, and the values $\alpha_m^{(H)}$ and $\alpha_m^{(L)}$ are determined by the noise-balancing process.

Next method 900 proceeds to process 950. In process 950 the material decomposition is performed, wherein new values for the projection lengths $L_1$ and $L_2$ are calculated.

Finally, at step 960, an inquiry is made into whether the stopping criteria have been satisfied. The stopping criteria can depend on convergence of the projection lengths $L_1$ and $L_2$, and whether the maximum number of loop iterations have been reached.

Figure 10:
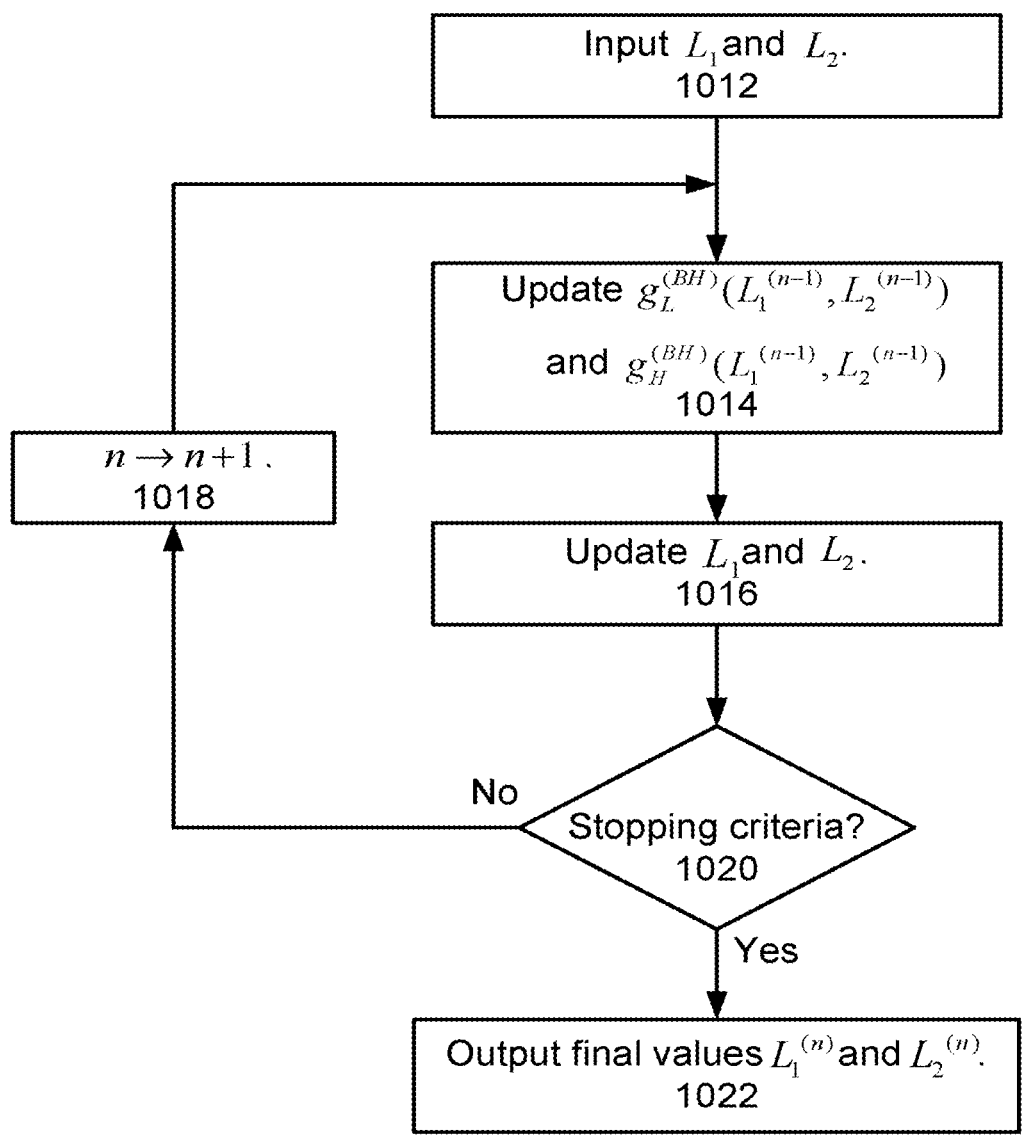
FIG. 10 shows a flow diagram of an implementation of a projection-domain material decomposition process.

The material decomposition process 950 can be an iterative process—as shown in FIG. 10—with its own stopping criteria. This iterative process can be referred to as the small loop, in contrast to the large loop including steps 920 through 960.

In one implementation, process 950 is performed according to the method shown in FIG. 10, as discussed in U.S. Pat. No. 8,194,961, incorporated herein by reference in its entirety. Similar to the detector counts for the high- and low-energy components, the high and low spectra can be given by $$S_H(E) = \sum_m a_m^{(H)} S_{air}(E), \text{ and}$$

$$S_L(E) = \sum_m a_m^{(L)} S_{air}(E),$$

wherein $S_H(E)$ and $S_L(E)$ are respectively the detected high- and low-energy spectra in the absence of the object OBJ (i.e., the object OBJ is air), and where $S_H(E)$ and $S_L(E)$ have been normalized such that $$\int dE \, S_H(E) = \int dE S_L(E) = 1.$$

By taking the natural logarithm of the detector counts, the log-projection data can be obtained as $$g_H(l) = -\ln(N_H/N_H^{air}) \text{ and}$$

$$g_L(l) = -\ln(N_L/N_L^{air}).$$

In one implementation, $L_1$ and $L_2$ are found using perturbation theory by treating the variations around the mean of the attenuation coefficients $\mu_1(E)$ and $\mu_2(E)$ as perturbations. First, the mean attenuation for the high- and low-energy spectra are given by $$\bar{\mu}_{1,2}^{H,L} = \int S_{H,L}(E) \mu_{1,2}(E) dE,$$

and the variations around the mean are given by $$\Delta\mu_{1,2}^{H,L}(E) = \mu_{1,2}(E) - \bar{\mu}_{1,2}^{H,L}.$$

Thus, the log-projection data can be expressed as $$g_H(l) = -\ln \int S_H(E) \exp[-\bar{\mu}_1^H L_1(l) - \Delta\mu_1^H(E) L_1(l) - \bar{\mu}_2^H L_2(l) - \Delta\mu_2^H(E) L_2(l)] dE$$

$$g_L(l) = -\ln \int S_L(E) \exp[-\bar{\mu}_1^L L_1(l) - \Delta\mu_1^L(E) L_1(l) - \bar{\mu}_2^L L_2(l) - \Delta\mu_2^L(E) L_2(l)] dE.$$

Simplifying these expressions, the log-projection data can be written as $$g_H(l) = \bar{\mu}_1^H L_1(l) + \bar{\mu}_2^H L_2(l) - g_H^{(BH)}(L_1(l), L_2(l))$$

$$g_L(l) = \bar{\mu}_1^L L_1(l) + \bar{\mu}_2^L L_1(l) - g_L^{(BH)}(L_1(l), L_2(l))$$

wherein $$g_{H,L}^{(BH)}(L_1(l), L_2(l)) = \ln \int S_{H,L}(E) \exp[-L_1(l)\Delta\mu_1^{H,L}(E) - L_2(l)\Delta\mu_2^{H,L}(E)]dE$$

is the beam-hardening perturbation.

The first step 1012 of process 950 initializes the iteration variable to n=0 and also initializes the values of the projection lengths $L_1$ and $L_2$. In one implementation, the initial values of the projection lengths are the same values used for the detector response correction calculation in step 920. In another implementation, the initial values of the projection lengths are the zeroth-order perturbation values calculated by solving the matrix equation $$\begin{pmatrix} g_H \\ g_L \end{pmatrix} = \begin{pmatrix} \bar{\mu}_1^H & \bar{\mu}_2^H \\ \bar{\mu}_1^L & \bar{\mu}_2^L \end{pmatrix} \begin{pmatrix} L_1 \\ L_2 \end{pmatrix}$$

to obtain $$\begin{pmatrix} L_1 \\ L_2 \end{pmatrix} = D^{-1} \begin{pmatrix} \bar{\mu}_2^L & -\bar{\mu}_2^H \\ -\bar{\mu}_1^L & \bar{\mu}_1^H \end{pmatrix} \begin{pmatrix} g_H \\ g_L \end{pmatrix}$$

wherein D is the determinant $D = \bar{\mu}_1^H \bar{\mu}_2^L - \bar{\mu}_1^L \bar{\mu}_2^H$.

The second step 1014 of process 950, which is also the first step in the iterative loop, updates the beam-hardening perturbation values using the $n^{th}$ order perturbation in the equation $$g_{H,L}^{(BH)}(L_1(l), L_2(l)) = \ln \int S_{H,L}(E) \exp[-L_1(l)\Delta\mu_1^{H,L}(E) - L_2(l)\Delta\mu_2^{H,L}(E)]dE.$$

The third step 1016 of process 950 is to update the values of $L_1$ and $L_2$ by solving for the $n+1^{th}$ perturbation by solving the matrix equation $$\begin{pmatrix} g_H + g_H^{(BH)}(L_1, L_2) \\ g_L + g_L^{(BH)}(L_1, L_2) \end{pmatrix} = \begin{pmatrix} \bar{\mu}_1^H & \bar{\mu}_2^H \\ \bar{\mu}_1^L & \bar{\mu}_2^L \end{pmatrix} \begin{pmatrix} L_1 \\ L_2 \end{pmatrix}$$

to obtain $$\begin{pmatrix} L_1^n \\ L_2^n \end{pmatrix} = D^{-1} \begin{pmatrix} \bar{\mu}_2^L & -\bar{\mu}_2^H \\ -\bar{\mu}_1^L & \bar{\mu}_1^H \end{pmatrix} \begin{pmatrix} g_H + g_H^{(BH)}(L_1^{n-1}, L_2^{n-1}) \\ g_L + g_L^{(BH)}(L_1^{n-1}, L_2^{n-1}) \end{pmatrix}.$$

After step 1018, step 1020 of process 950 inquiries whether the stopping criteria have been satisfied. In one implementation, the stopping criteria are satisfied when the values $L_1$ and $L_2$ satisfy a predetermined convergence criteria, such as whether the difference between each current and previous values of $L_1$ and $L_2$ are less than a predefined threshold. The stopping criteria can also be conditioned on whether a maximum number of iterations have been reached. If stopping criteria have not been satisfied, then the loop variable n is incremented at step 1018 and the loop begins again starting from step 1014.

Figure 11:
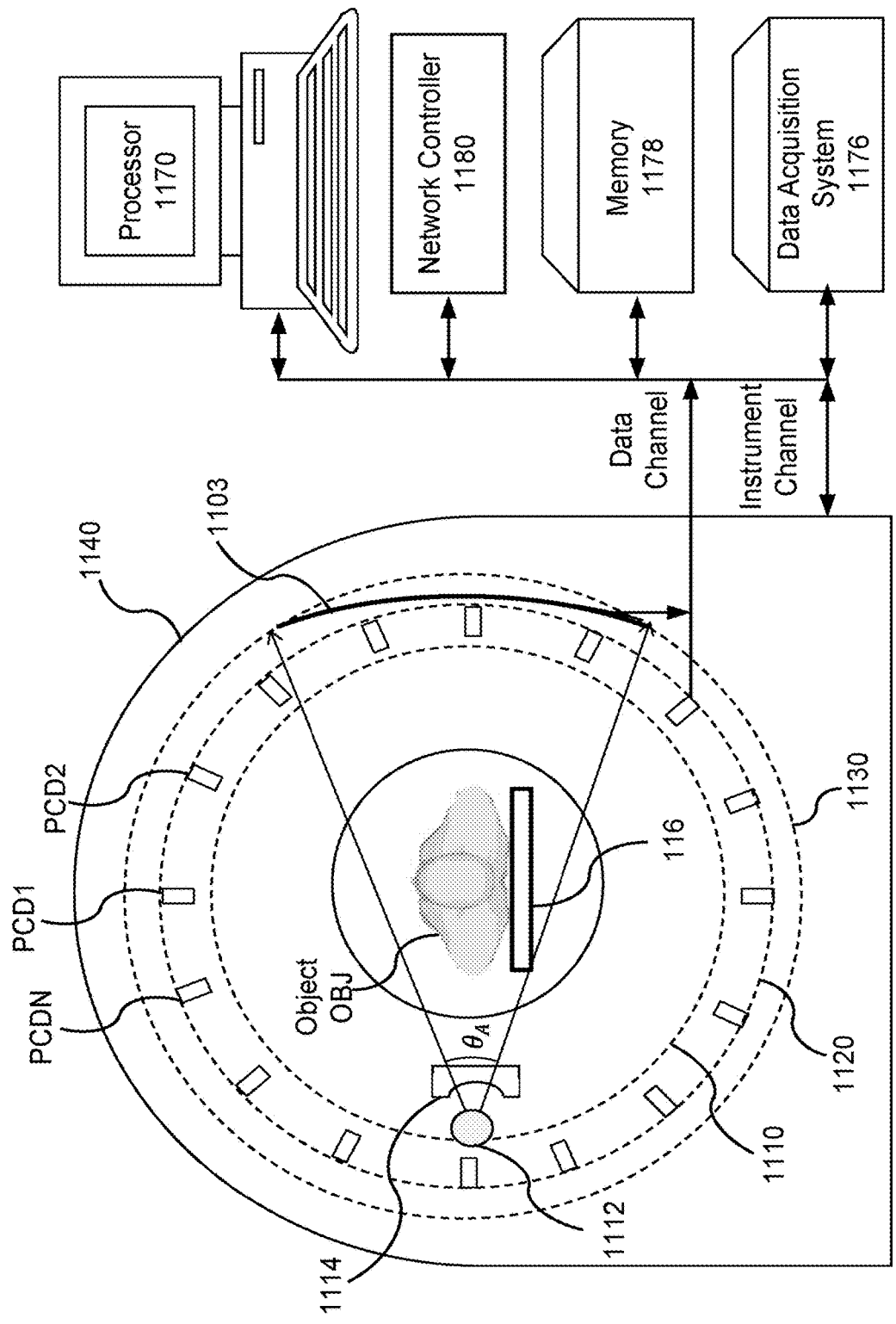
FIG. 11 shows a schematic diagram of an implementation of an X-ray CT apparatus having photon-counting detectors arranged in a fourth-generation geometry and energy-integrating detectors (PCDs) arranged in a third-generation geometry, the CT apparatus further including control, processing, and data-acquisition circuitry.

FIG. 11 shows a computed tomography (CT) scanner having both energy-integrating detectors arranged in a third-generation geometry and PCDs arranged in a fourth-generation geometry. Illustrated in FIG. 11 is an implementation for placing the PCDs in a predetermined fourth-generation geometry in combination with a detector unit 1103 in a predetermined third-generation geometry in a CT scanner system. The diagram illustrates relative positions among the X-ray source 1112, the collimator/filter 1114, the X-ray detector 1103, and the photon-counting detectors PCD1 through PCDN.

Also shown in FIG. 11 is circuitry and hardware for acquiring, storing, processing, and distributing X-ray projection data. The circuitry and hardware include: a processor 1170, a network controller 1180, a memory 1178, and a data acquisition system 1176.

In one alternative implementation, the CT scanner includes PCDs but does not include the energy-integrating detector unit 1103.

As the X-ray source 1112 and the detector unit 1103 are housed in a gantry 1140 and rotate around circular paths 1110 and 130 respectively, the photon-counting detectors PCDs and the detector unit 1103 respectively detects the transmitted X-ray radiation during data acquisition. The photon-counting detectors PCD1 through PCDN intermittently detect the X-ray radiation that has been transmitted and individually output a count value representing a number of photons, for each of the predetermined energy bins. On the other hand, the detector elements in the detector unit 1103 continuously detect the X-ray radiation that has been transmitted and output the detected signals as the detector unit 1103 rotates. In one implementation, the detector unit 1103 has densely placed energy-integrating detectors in predetermined channel and segment directions on the detector unit surface.

In one implementation, the X-ray source 1112, the PCDs and the detector unit 1103 collectively form three predetermined circular paths that differ in radius. At least one X-ray source 1112 rotates along a first circular path 1110 while the photon-counting detectors are sparsely placed along a second circular path 120. Further, the detector unit 1103 travels along a third circular path 130. The first circular path 1110, second circular path 120, and third circular path 130 can be determined by annular rings that are rotatably mounted to the gantry 1140.

There are other alternative embodiments for placing the photon-counting detectors in a predetermined fourth-generation geometry in combination with the detector unit in a predetermined third-generation geometry in the CT scanner. Several alternative embodiments of the X-ray CT Scanner as described in U.S. patent application Ser. No. 13/029,1097, herein incorporated by reference in its entirety.

In one implementation, the X-ray source 1112 is optionally a single energy source. In another implementation, the X-ray source 1112 is configured to perform a kV-switching function for emitting X-ray radiation at a predetermined high-level energy and at a predetermined low-level energy. In still another alternative embodiment, the X-ray source 1112 is a single source emitting a broad spectrum of X-ray energies. In still another embodiment, the X-ray source 1112 includes multiple X-ray emitters with each emitter being spatially and spectrally distinct.

The detector unit 1103 can use energy-integrating detectors such as scintillation elements with photo-multiplier tubes or avalanche photo-diodes to detect the resultant scintillation photons from scintillation events resulting from the X-ray radiation interacting with the scintillator elements. The scintillator elements can be crystalline, an organic liquid, a plastic, or other know scintillator.

The PCDs can use a direct X-ray radiation detectors based on semiconductors, such as cadmium telluride (CdTe), cadmium zinc telluride (CZT), silicon (Si), mercuric iodide ($HgI_2$), and gallium arsenide (GaAs).

The CT scanner also includes a data channel that routes projection measurement results from the photon-counting detectors and the detector unit 1103 to a data acquisition system 1176, a processor 1170, memory 1178, network controller 1180. The data acquisition system 1176 controls the acquisition, digitization, and routing of projection data from the detectors. The data acquisition system 1176 also includes radiography control circuitry to control the rotation of the annular rotating frames 1110 and 130. In one implementation data acquisition system 1176 will also control the movement of the bed 1116, the operation of the X-ray source 1112, and the operation of the X-ray detectors 1103. The data acquisition system 1176 can be a centralized system or alternatively it can be a distributed system. In an implementation, the data acquisition system 1176 is integrated with the processor 1170. The processor 1170 performs functions including reconstructing images from the projection data, pre-reconstruction processing of the projection data, and post-reconstruction processing of the image data. The processor 1170 also performs the functions and methods described herein, including: method 300, 400, 500, 600, 800, and 900.

The pre-reconstruction processing of the projection data can include correcting for detector calibrations, detector nonlinearities, polar effects, and noise balancing. Post-reconstruction processing can include filtering and smoothing the image, volume rendering processing, and image difference processing as needed. The image reconstruction process can be performed using filtered back projection, iterative image reconstruction methods, or stochastic image reconstruction methods. Both the processor 1170 and the data acquisition system 1176 can make use of the memory 1176 to store, e.g., projection data, reconstructed images, calibration data and parameters, and computer programs.

The processor 1170 can include a CPU that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the memory may be non-volatile, such as ROM, EPROM, EEPROM or FLASH memory. The memory can also be volatile, such as static or dynamic RAM, and a processor, such as a microcontroller or microprocessor, may be provided to manage the electronic memory as well as the interaction between the FPGA or CPLD and the memory.

Alternatively, the CPU in the reconstruction processor may execute a computer program including a set of computer-readable instructions that perform the functions described herein, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, such as a Xenon processor from Intel of America or an Opteron processor from AMD of America and an operating system, such as Microsoft VISTA, UNIX, Solaris, LINUX, Apple, MAC-OS and other operating systems known to those skilled in the art. Further, CPU can be implemented as multiple processors cooperatively working in parallel to perform the instructions.

In one implementation, the reconstructed images can be displayed on a display. The display can be an LCD display, CRT display, plasma display, OLED, LED or any other display known in the art. The memory 1178 can be a hard disk drive, CD-ROM drive, DVD drive, FLASH drive, RAM, ROM or any other electronic storage known in the art.

The network controller 1180, such as an Intel Ethernet PRO network interface card from Intel Corporation of America, can interface between the various parts of the CT scanner. Additionally, the network controller 1180 can also interface with an external network. As can be appreciated, the external network can be a public network, such as the Internet, or a private network such as an LAN or WAN network, or any combination thereof and can also include PSTN or ISDN sub-networks. The external network can also be wired, such as an Ethernet network, or can be wireless such as a cellular network including EDGE, 3G and 4G wireless cellular systems. The wireless network can also be WiFi, Bluetooth, or any other wireless form of communication that is known.

While certain implementations have been described, these implementations have been presented by way of example only, and are not intended to limit the teachings of this disclosure. Indeed, the novel methods, apparatuses and systems described herein may be embodied in a variety of other forms; furthermore, various omissions, substitutions and changes in the form of the methods, apparatuses and systems described herein may be made without departing from the spirit of this disclosure.

The invention claimed is:

1. An apparatus, comprising:
   processing circuitry configured to
      obtain first projection data having a plurality of energy components, the first projection data representing total counts including single X-ray detection events and multiple X-ray detection events, the total counts representing an intensity of X-ray radiation having been transmitted through an object and then detected at a plurality of energy-resolving detector elements;
      obtain second projection data having the plurality of energy components, wherein the second projection data represents singles counts of the single X-ray detection events, the singles counts representing the intensity of X-ray radiation having been transmitted through the object and then detected at the plurality of energy-resolving detector elements; and
      determine a material decomposition by
         estimating a first pair of projection lengths using a material decomposition of the first projection data, the first pair of projection lengths being a solution of a first material-decomposition method, and
         estimating a second pair of projection lengths using a material decomposition of the second projection data, the second pair of projection lengths being a solution of a second material-decomposition method.

2. The apparatus of claim 1, wherein the processing circuitry is further configured to determine the material decomposition with
   the first material-decomposition method being one of a cost-function method and a split step method, and
   the second material-decomposition method being one of a cost-function method and a split step method.

3. The apparatus of claim 1, wherein the processing circuitry is further configured to determine the material decomposition by
   determining a search region around the first pair of projection lengths using predefined criteria, and
   the second material-decomposition method is constrained to maintain the second pair of projection lengths within the search region.

4. The apparatus of claim 3, wherein the processing circuitry is further configured to determine the material decomposition by
   the second material-decomposition method starting a search to estimate the second pair of projection lengths at the first pair of projection lengths.

5. The apparatus of claim 1, wherein the processing circuitry is further configured to determine the material decomposition by
   estimating a plurality of pairs of projection lengths that are respectively solutions of the second material-decomposition method, the plurality of pairs of projection lengths including the second pair of projection lengths,
   determining distances between the first pair of projection lengths and respective pairs of the plurality of pairs of projection lengths, and
   selecting, as the material-decomposition, a pair of projection lengths of the plurality of pairs of projection lengths corresponding to a shortest distance of the distances.

6. The apparatus of claim 5, wherein the processing circuitry is further configured to determine the material decomposition by
   determining the distances using a Euclidean distance measure.

7. An apparatus, comprising:
   processing circuitry configured to
      obtain first projection data having a plurality of energy components, the first projection data representing total counts including single X-ray detection events and multiple X-ray detection events, the total counts representing X-ray radiation detected at a plurality of energy-resolving detector elements;
      obtain second projection data having a plurality of energy components, wherein the second projection data represents singles counts of the single X-ray detection events, the singles counts representing the X-ray radiation detected at the plurality of energy-resolving detector elements; and
      determine a material decomposition by
         estimating a plurality of pairs of projection lengths using a material decomposition of the second projection data, each of the plurality of pairs of projection lengths locally optimizing a material-decomposition method; and
         generating a plurality of estimates of the first projection data using the plurality of pairs of projection lengths to determine an attenuation of the X-ray radiation, and
         selecting, as the material-decomposition, a pair of the plurality of pairs of projection lengths corresponding to an estimate of the plurality of estimates of the first projection data that is closest to the first projection data.

8. The apparatus of claim 7, wherein the processing circuitry is further configured to determine the material decomposition by
   determining which of the plurality of estimates of the first projection data is closest to the first projection data using a cost function that includes at least one distance measure, and
   the least one distance measure includes at least one of a least squares distance measure, a weighted least squares distance measure, and a Poisson likelihood distance measure.

9. The apparatus of claim 7, wherein the processing circuitry is further configured to determine the material decomposition by
   estimating the plurality of pairs of projection lengths using the material-decomposition method, which is one of a cost-function method and a split-step method.

10. The apparatus of claim 7, wherein the processing circuitry is further configured to estimate the plurality of pairs of projection lengths by
   optimizing a first pair of projection lengths of the plurality of pairs of projection lengths using optimization,
   generating an exclusion region in a region along a search path of the optimizing of the first pair of projection lengths, and
   optimizing a second pair of projection lengths of the plurality of pairs of projection lengths using optimization that is constrained to exclude the exclusion region, and
   expanding the exclusion region, when the optimizing of the second pair of projection lengths converges to the first pair of projection lengths, to include all optimization search paths converging to the first pair of projection lengths, and continuing the optimizing of the second pair of projection lengths constrained to exclude the exclusion region, until convergence to a second pair of projection lengths that is different from the first pair of projection lengths.

11. An apparatus, comprising:
   processing circuitry configured to
      obtain first projection data, the first projection data representing integrated energies of X-ray radiation detected at a plurality of energy integrating detector elements;
      obtain second projection data having a plurality of energy components, wherein the second projection data represents singles counts, the singles counts representing detection events of single X-ray photons detected at a plurality of energy-resolving detector elements; and
      determine a pair of projection lengths using a combined material decomposition of the second projection data and the first projection data, wherein
      the pair of projection lengths optimize a combined cost function that uses a first distance measure between the first projection data and a model of the first projection data and uses a second distance measure between the second projection data and a model of the second projection data.

12. The apparatus of claim 11, wherein the processing circuitry is further configured to determine the pair of projection lengths by optimizing the pair of projection lengths to minimize the combined cost function, wherein
   the combined cost function includes a linear superposition of the first distance measure between the first projection data and a model of the first projection data measure and the second distance measure between the second projection data and a model of the second projection data, the first distance measure including at least one of a least squares distance measure, a weighted least squares distance measure, and a Poisson-likelihood distance measure, and the second distance measure including at least one of a least squares distance measure, a weighted least squares distance measure, and a Poisson-likelihood distance measure.

13. The apparatus of claim 11, wherein the processing circuitry is further configured to determine the pair of projection lengths by optimizing the pair of projection lengths using the model of the second projection data that accounts for absorption along X-ray trajectories using the pair of projection lengths, and optimizing the pair of projection lengths using the model of the first projection data that accounts for absorption along X-ray trajectories using the pair of projection lengths.

14. The apparatus of claim 13, wherein the processing circuitry is further configured to determine the pair of projection lengths by optimizing the pair of projection lengths using a global optimization method.

15. An apparatus, comprising:
an X-ray source radiating X-rays;
a plurality of detector elements each configured to
  detect a plurality of energy components of the X-rays that are radiated from the X-ray source,
  generate first projection data representing total counts including a combination of single X-ray detection events and multiple X-ray detection events at each of the plurality of detector elements, and
  generate second projection data representing singles counts including the single X-ray detection events at each of the plurality of detector elements; and
processing circuitry configured to
  determine a material decomposition by
    estimating a first pair of projection lengths using a material decomposition of the first projection data, the first pair of projection lengths being a solution of a first material-decomposition method, and
    estimating a second pair of projection lengths using a material decomposition of the second projection data, the second pair of projection lengths being a solution of a second material-decomposition method.

16. The apparatus of claim 15, wherein the processing circuitry is further configured to determine the material decomposition by determining a search region around the first pair of projection lengths using predefined criteria, and the second material-decomposition method is constrained to maintain the second pair of projection lengths within the search region.

17. The apparatus of claim 16, wherein the processing circuitry is further configured to determine the material decomposition by estimating a plurality of pairs of projection lengths that locally optimize the second material-decomposition method, the plurality of pairs of projection lengths including the second pair of projection lengths, determining distances between the first pair of projection lengths and respective pairs of the plurality of pairs of projection lengths, and selecting, as the material-decomposition, a pair of projection lengths of the plurality of pairs of projection lengths corresponding to a shortest distance of the distances.

18. The apparatus of claim 15, wherein the processing circuitry is further configured to determine the material decomposition by the first material-decomposition method being one of a cost-function method and a split step method, and the second material-decomposition method being one of a cost-function method and a split step method.

19. A method, comprising:

obtaining first projection data having a plurality of energy components, the first projection data representing total counts including single X-ray detection events and multiple X-ray detection events, the total counts representing an intensity of X-ray radiation having been transmitted through an object and then detected at a plurality of energy-resolving detector elements;

obtaining second projection data having the plurality of energy components, wherein the second projection data represents singles counts of the single X-ray detection events, the singles counts representing the intensity of X-ray radiation having been transmitted through the object and then detected at the plurality of energy-resolving detector elements; and determining a material decomposition by estimating a first pair of projection lengths using a material decomposition of the first projection data, the first pair of projection lengths being a solution of a first material-decomposition method, and estimating a second pair of projection lengths using a material decomposition of the second projection data, the second pair of projection lengths being a solution of a second material-decomposition method.

20. A non-transitory computer readable storage medium including executable instruction, wherein the instructions, when executed by circuitry, cause the circuitry to perform the method according to claim 19.

* * * * *